(12) United States Patent
Kim et al.

(10) Patent No.: US 10,968,410 B2
(45) Date of Patent: Apr. 6, 2021

(54) METHOD AND APPARATUS FOR SYNTHESIZING METHANE GAS FROM CARBON DIOXIDE AND HYDROGEN AT ROOM TEMPERATURE AND ATMOSPHERIC PRESSURE

(71) Applicant: INDUSTRY-ACADEMIC COOPERATION FOUNDATION CHOSUN UNIVERSITY, Gwangju (KR)

(72) Inventors: Tae Gyu Kim, Gwangju (KR); Chung Jun Lee, Gwangju (KR)

(73) Assignee: INDUSTRY-ACADEMIC COOPERATION FOUNDATION CHOSUN UNIVERSITY, Gwangju (KR)

( * ) Notice: Subject to any disclaimer, the term of this patent is extended or adjusted under 35 U.S.C. 154(b) by 582 days.

(21) Appl. No.: 15/540,613

(22) PCT Filed: Nov. 16, 2016

(86) PCT No.: PCT/KR2016/013218
§ 371 (c)(1),
(2) Date: Jun. 29, 2017

(87) PCT Pub. No.: WO2017/090933
PCT Pub. Date: Jun. 1, 2017

(65) Prior Publication Data
US 2017/0355919 A1 Dec. 14, 2017

(30) Foreign Application Priority Data

Nov. 26, 2015 (KR) .................. 10-2015-0166191

(51) Int. Cl.
*C10L 3/08* (2006.01)
*B01J 19/08* (2006.01)
(Continued)

(52) U.S. Cl.
CPC .............. *C10L 3/08* (2013.01); *B01J 12/00* (2013.01); *B01J 19/088* (2013.01); *C07C 1/12* (2013.01);
(Continued)

(58) Field of Classification Search
None
See application file for complete search history.

(56) References Cited

U.S. PATENT DOCUMENTS

2011/0048251 A1* 3/2011 Bardenshtein ...... C23C 16/4415
99/451
2014/0364517 A1* 12/2014 Selstam ..................... C10J 3/18
518/704

FOREIGN PATENT DOCUMENTS

EP 3050865 A1 * 8/2016
KR 10-0561166 B1 3/2006
(Continued)

OTHER PUBLICATIONS

Garbarino et al., "Methanation of carbon dioxide on Ru/Al2O3: Catalytic activity and infrared study", Catalysis Today 277 (2016) 21-28.*
(Continued)

*Primary Examiner* — Kishor Mayekar
(74) *Attorney, Agent, or Firm* — The PL Law Group, PLLC

(57) ABSTRACT

A methane ($CH_4$) gas is synthesized from carbon dioxide ($CO_2$) and hydrogen ($H_2$) using catalyst-dielectric barrier discharge (DBD) plasma at room temperature and atmospheric pressure. In the method and apparatus for synthesizing methane gas of the invention, methane ($CH_4$) gas, which is synthetic natural gas, can be effectively synthesized only from carbon dioxide ($CO_2$) and hydrogen ($H_2$) using DBD plasma at room temperature and atmospheric pressure, and also, additional heating and pressurization devices are (Continued)

not used during the methane gas synthesis process, thus reducing production costs and realizing high-value-added processing due to the absence of risks during the processing.

4 Claims, 9 Drawing Sheets

(51) Int. Cl.
    *B01J 12/00*     (2006.01)
    *C07C 1/12*     (2006.01)
    *C10L 3/10*     (2006.01)

(52) U.S. Cl.
    CPC .......................... *B01J 2219/0805* (2013.01); *B01J 2219/0869* (2013.01); *B01J 2219/0883* (2013.01); *B01J 2219/0892* (2013.01); *B01J 2219/0896* (2013.01); *C07C 2521/04* (2013.01); *C07C 2523/46* (2013.01); *C10L 3/101* (2013.01); *C10L 3/104* (2013.01); *C10L 3/105* (2013.01); *C10L 2290/38* (2013.01)

(56) References Cited

FOREIGN PATENT DOCUMENTS

| | | |
|---|---|---|
| KR | 10-2008-0060739 A | 7/2008 |
| KR | 10-2012-0090067 A | 8/2012 |
| KR | 10-2013-0033536 A | 4/2013 |
| KR | 10-2014-0080661 A | 7/2014 |
| WO | WO 2015/011503 * | 1/2015 |

OTHER PUBLICATIONS

International Search Report for PCT/KR2016/013218.

* cited by examiner

METHOD AND APPARATUS FOR SYNTHESIZING METHANE GAS FROM CARBON DIOXIDE AND HYDROGEN AT ROOM TEMPERATURE AND ATMOSPHERIC PRESSURE

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/013218, filed Nov. 16, 2016, which claims priority to the benefit of Korean Patent Application No. 10-2015-0166191 filed in the Korean Intellectual Property Office on Nov. 26, 2015, the entire contents of which are incorporated herein by reference.

TECHNICAL FIELD

The present invention relates to a method and apparatus for synthesizing methane gas from carbon dioxide and hydrogen at room temperature and atmospheric pressure, and more particularly to a method of synthesizing methane ($CH_4$) gas as synthetic natural gas only from carbon dioxide ($CO_2$) and hydrogen ($H_2$) using catalyst-dielectric barrier discharge (DBD) plasma at room temperature and atmospheric pressure.

BACKGROUND ART

Natural gas is regarded as the cleanest fuel for use in power generation, heating and vehicles, and is thus of great use. However, naturally occurring natural gas is in limited supply, and processes for synthesizing natural gas are becoming a high-value-added industry.

Recently, a technique for synthesizing a liquid hydrocarbon compound by mixing carbon monoxide (CO) and hydrogen is exemplified by a Fischer-Tropsch process. This process first began in 1923 with the development of a technique for producing synthetic fuel from syngas through coal gasification by the German chemists Fischer and Tropsch.

The Fischer-Tropsch process is mainly performed using a metal catalyst such as cobalt (Co) or iron (Fe) at a temperature of 150° C. or more and a pressure of 10 atm or more.

However, the Fischer-Tropsch process requires an additional heating device and an additional pressurization device for applying pressure, and may suffer from increased processing costs and maintenance costs and from difficulties and risks encountered during the processing.

Also, thorough research is ongoing these days into a variety of synthesis methods using carbon dioxide in lieu of carbon monoxide in order to remove or recycle carbon dioxide, which is receiving attention as a global greenhouse gas.

Therefore, there is a need to develop a novel technique for producing synthetic natural gas, which is able to contribute to environmentally friendly techniques as well as a reduction in global warming due to the removal of carbon dioxide, and is also considered a high-value-added technique.

SUMMARY

Intensive and thorough research carried out by the present inventors aiming to solve the problems encountered in the related art has led to the development of a process of synthesizing methane only from carbon dioxide and hydrogen at room temperature and atmospheric pressure, in lieu of existing processes of producing synthetic natural gas such as methane using carbon monoxide, water, hydrogen and the like at high temperature and high pressure, thus culminating in the present invention.

Therefore, an object of the present invention is to provide a method and apparatus for synthesizing methane ($CH_4$) gas as synthetic natural gas only from carbon dioxide ($CO_2$) and hydrogen ($H_2$) using catalyst-dielectric barrier discharge (DBD) plasma at room temperature and atmospheric pressure.

In addition, another object of the present invention is to provide a method and apparatus for synthesizing methane ($CH_4$), in which additional heating and pressurization devices are not used during the methane gas synthesis process, thus reducing production and maintenance costs, overcoming processing and operation difficulties, and realizing high-value-added methane gas synthesis on a variety of target platforms due to the absence of risks during the processing.

The objects of the present invention are not limited to the foregoing, and other objects not mentioned herein will be able to be clearly understood by those skilled in the art from the following description.

In order to accomplish the above objects, the present invention provides a method of synthesizing methane gas from carbon dioxide and hydrogen at room temperature under atmospheric pressure, comprising: a gas supply step of supplying carbon dioxide ($CO_2$) gas and hydrogen ($H_2$) gas to a reactor containing a catalyst; a methane gas synthesis step of synthesizing methane ($CH_4$) gas by forming plasma on the catalyst in the reactor at room temperature and atmospheric pressure; and a separation step of separating the synthesized methane gas, wherein, in the methane gas synthesis step, ionization of the carbon dioxide and the hydrogen is promoted by the plasma and synthesis of the methane gas from the carbon dioxide and the hydrogen is promoted by the catalyst.

In a preferred embodiment, the catalyst may be a Ru/γ-$Al_2O_3$ catalyst configured such that a gamma-alumina support is impregnated with ruthenium (Ru).

In a preferred embodiment, the plasma is dielectric barrier discharge (DBD) plasma.

In a preferred embodiment, the gas supply step comprises supplying nitrogen ($N_2$) or argon (Ar) gas to form the DBD plasma.

In a preferred embodiment, the separation step comprises recovering and re-supplying carbon dioxide, hydrogen, nitrogen and argon, which remain without being used for the synthesis of the methane gas.

In addition, the present invention provides an apparatus for synthesizing methane gas from carbon dioxide and hydrogen at room temperature under atmospheric pressure, comprising: a gas supply unit for supplying carbon dioxide ($CO_2$) gas and hydrogen ($H_2$) gas; a reactor configured to contain a catalyst and to synthesize methane ($CH_4$) gas from the carbon dioxide gas and the hydrogen gas by forming plasma at room temperature and atmospheric pressure; and a separation unit for separating the synthesized methane gas.

In a preferred embodiment, the catalyst comprises any one selected from the group consisting of ruthenium (Ru), rhodium (Rh), cobalt (Co), and platinum (Pt). Also, a Group 8 metal element may be used as the catalyst.

In a preferred embodiment, the reactor is a catalyst-DBD (Dielectric Barrier Discharge) plasma hybrid reactor, comprising: a quartz glass tube having a gas inlet in an upper portion thereof and an outlet in a lower portion thereof; an inner electrode having a cylindrical rod shape and provided in the quartz glass tube; an outer electrode wound around the outer surface of the quartz glass tube; and a catalyst contained in the quartz glass tube between the inner electrode and the outer electrode.

In a preferred embodiment, the inner electrode is composed of a stainless steel material and the outer electrode is composed of iron (Fe).

In a preferred embodiment, the apparatus further comprises a high-voltage supplier for applying high voltage to the inner electrode and the outer electrode so as to discharge plasma.

In a preferred embodiment, the gas supply unit further supplies nitrogen ($N_2$) or argon (Ar) gas to form the DBD plasma.

In a preferred embodiment, the separation unit further comprises: a methane gas separation recovery part for separating and recovering the synthesized methane gas; a gas separation part for recovering and re-supplying carbon dioxide, hydrogen, nitrogen and argon, remaining without being used for the synthesis of the methane gas; and a liquid separation part for separating and removing a liquid hydrocarbon material.

The present invention has the following superior effects.

In a method and apparatus for synthesizing methane gas according to the present invention, methane ($CH_4$) gas, which is synthetic natural gas, can be effectively synthesized only from carbon dioxide ($CO_2$) and hydrogen ($H_2$) using catalyst-dielectric barrier discharge (DBD) plasma at room temperature and atmospheric pressure.

Also, in the method and apparatus for synthesizing methane gas according to the present invention, additional heating and pressurization devices are not used during the methane gas synthesis process, thus reducing production costs and realizing high-value-added processing due to the absence of risks during the processing.

DETAILED DESCRIPTION

Figure 1:
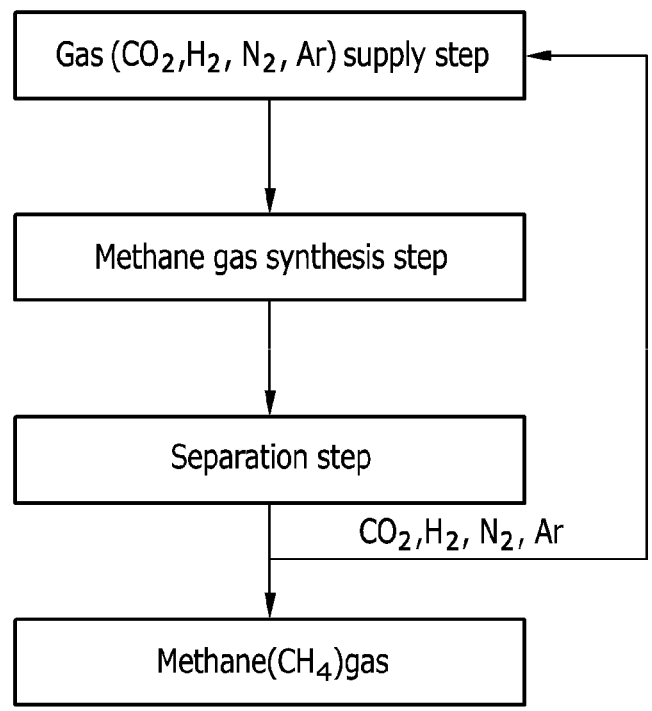
FIG. 1 shows a process of synthesizing methane gas from carbon dioxide and hydrogen at room temperature and atmospheric pressure according to an embodiment of the present invention.

Although the terms used in the present invention are selected from among generally known and used terms, some of the terms mentioned in the description of the present invention have been selected by the applicant, the detailed meanings of which should be understood not simply by the actual terms used but by the meaning of each term in the context of the detailed description of the invention or in consideration of the meanings used.

Hereinafter, a detailed description will be given of the technical configuration of the present invention with reference to preferred embodiments illustrated in the appended drawings.

However, the present invention is not limited to the embodiments described herein but may be embodied in other forms. Like reference numerals used to describe the present invention throughout the specification denote like elements.

FIG. 1 shows a process of synthesizing methane gas from carbon dioxide and hydrogen at room temperature and atmospheric pressure according to an embodiment of the present invention.

As shown in FIG. 1, the method of synthesizing methane gas from carbon dioxide and hydrogen at room temperature and atmospheric pressure according to the embodiment of the present invention largely includes a gas supply step, a methane gas synthesis step and a separation step, and is technically characterized in that the synthesis of methane gas is carried out at room temperature and atmospheric pressure and also in that methane ($CH_4$) gas, which is synthetic natural gas, may be synthesized only from carbon dioxide ($CO_2$) and hydrogen ($H_2$) using catalyst-dielectric barrier discharge (DBD) plasma.

In the gas supply step, carbon dioxide gas and hydrogen gas, which are directly used for a methane gas synthesis reaction, are supplied. The method of synthesizing methane gas according to the embodiment of the present invention enables the synthesis of methane gas using only carbon dioxide and hydrogen, and obviates material such as carbon monoxide and the like.

In the gas supply step, nitrogen ($N_2$) or argon (Ar) gas may be supplied to form the dielectric barrier discharge plasma (hereinafter, referred to as "DBD plasma"). Here, such gas is preferably supplied to improve processing efficiency, but may be omitted depending on the processing circumstances, and DBD plasma discharge may be performed using only carbon dioxide and hydrogen.

In the gas supply step, the corresponding gases may be supplied into a catalyst-DBD plasma hybrid reactor 120 at predetermined flow rates using a gas mass flow controller through a pressure regulator from a 99.999%-high-purity-gas vessel, or may be supplied using an air-blowing device under the condition that a large amount of carbon dioxide is present in the air. The supplied gases may be blended in the pipe during the transfer into the catalyst-DBD plasma hybrid reactor, and are supplied at room temperature and atmospheric pressure because an additional pressurization or heating device is not used.

Subsequently, in the methane gas synthesis step, DBD plasma is formed in the catalyst-DBD plasma hybrid reactor at room temperature and atmospheric pressure, thus forming methane ($CH_4$) gas.

In the method of synthesizing methane gas according to the embodiment of the present invention, methane gas is synthesized from carbon dioxide and hydrogen through an interaction between the catalyst and the DBD plasma.

Specifically, radical production and ionization of carbon dioxide and hydrogen are promoted by the plasma, and also, the synthesis of methane gas from carbon dioxide and hydrogen is promoted by the catalyst.

The catalyst may include a Group 8 metal element such as ruthenium (Ru) or rhodium (Rh). Useful in an embodiment of the present invention is a Ru/$\gamma$-$Al_2O_3$ catalyst, configured such that a gamma alumina support is impregnated with ruthenium (Ru).

The DBD plasma has electrical insulating properties under normal conditions in which a dielectric barrier is disposed between electrodes, but may be uniformly distributed over the corresponding area while the flow of current is limited when at least one insulator enabling electrical polarization under an electric field is inserted and high voltage is applied. Depending on the properties of the dielectric barrier, the characteristics of the plasma may vary, and thus the effect thereof on a chemical reaction may also vary, which is utilized in the embodiment of the present invention. In the present invention, the DBD plasma enables not only the hybrid reactor 120 but also the ruthenium catalyst to act as the dielectric barrier, and such conditions may have a positive influence on the chemical reaction for synthesizing methane gas.

Due to the greater number of radicals formed by the DBD plasma, reactivity attributable to the ruthenium catalyst may be improved.

Thus, the DBD plasma and the catalyst or the catalyst and the DBD plasma have mutually complementary relationships and have a positive effect on each other, thereby maximizing the processing efficiency for methane gas synthesis.

The methane gas synthesis step is performed at room temperature and atmospheric pressure. As described above, due to the complementary characteristics between the DBD plasma and the catalyst or the catalyst and the DBD plasma, the synthesis of methane gas becomes possible at room temperature and atmospheric pressure, without the need to apply a high temperature or a high pressure.

Finally, in the separation step, the synthesized methane gas is separated and recovered.

In the separation step, a dewatering process using a silica trap may be performed to remove water, and carbon dioxide, hydrogen, nitrogen and argon, remaining without being used for methane gas synthesis, may be recovered and re-supplied to the gas supply unit. Furthermore, in the case where carbon monoxide (CO) or a liquid hydrocarbon material may be generated, it may be separated and removed.

MODE FOR INVENTION

Figure 2:
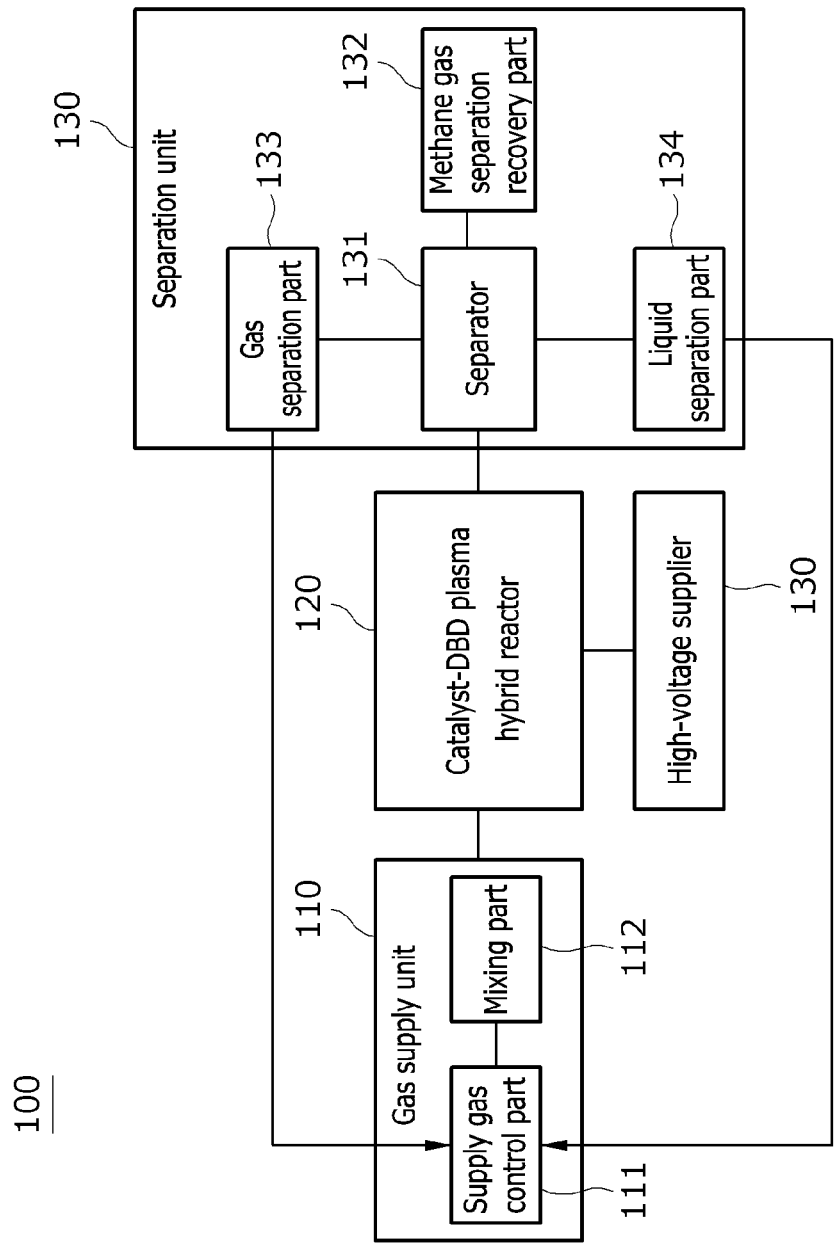
FIG. 2 shows an apparatus for synthesizing methane gas from carbon dioxide and hydrogen at room temperature and atmospheric pressure according to an embodiment of the present invention.

FIG. 2 shows an apparatus for synthesizing methane gas from carbon dioxide and hydrogen at room temperature and atmospheric pressure according to an embodiment of the present invention.

As shown in FIG. 2, the apparatus 100 for synthesizing methane gas from carbon dioxide and hydrogen at room temperature and atmospheric pressure according to the embodiment of the present invention largely includes a gas supply unit 110, a catalyst-DBD plasma hybrid reactor 120 and a separation unit 130, and is technically characterized in that synthesis of methane gas is carried out at room temperature and atmospheric pressure and also in that methane ($CH_4$) gas, which is synthetic natural gas, may be synthesized only from carbon dioxide ($CO_2$) and hydrogen ($H_2$) using catalyst-DBD plasma.

The gas supply unit 110 functions to supply carbon dioxide gas and hydrogen gas, which are directly used for a methane gas synthesis reaction. The apparatus for synthesizing methane gas according to the embodiment of the present invention enables the synthesis of methane gas using only carbon dioxide and hydrogen, and obviates material such as carbon monoxide and the like.

The gas supply unit 110 may include a supply gas control part 111 and a mixing part 112.

The supply gas control part 111 plays a role in controlling the flow rates of gases using a gas mass flow controller through a pressure regulator from a 99.999%-high-purity-gas vessel so as to supply such gases to the mixing part 112. The supplied gases are mixed in the mixing part 112 and then transferred into the catalyst-DBD plasma hybrid reactor. The gas supply unit 110 may supply gases at room temperature and atmospheric pressure without the use of an additional heating or pressurization device.

The gas supply unit 110 may also supply nitrogen ($N_2$) or argon (Ar) gas to form the DBD plasma. Here, such gas is preferably supplied to improve processing efficiency, but may be omitted depending on the processing circumstances, and DBD plasma discharge may be performed using only carbon dioxide and hydrogen.

The catalyst-DBD plasma hybrid reactor 120 may contain a catalyst, whereby DBD plasma is formed at room temperature and atmospheric pressure, thus synthesizing methane ($CH_4$) gas from the supplied carbon dioxide gas and hydrogen gas.

Figure 3:
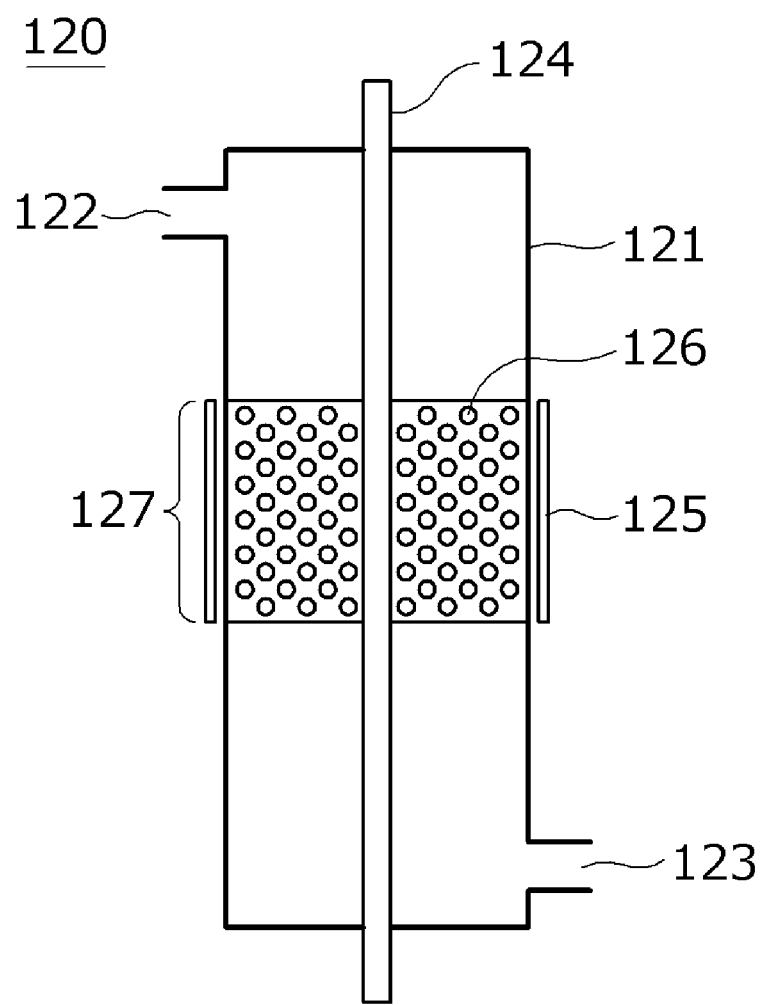
FIG. 3 shows a catalyst-DBD (Dielectric Barrier Discharge) plasma hybrid reactor according to an embodiment of the present invention.
Figure 4:
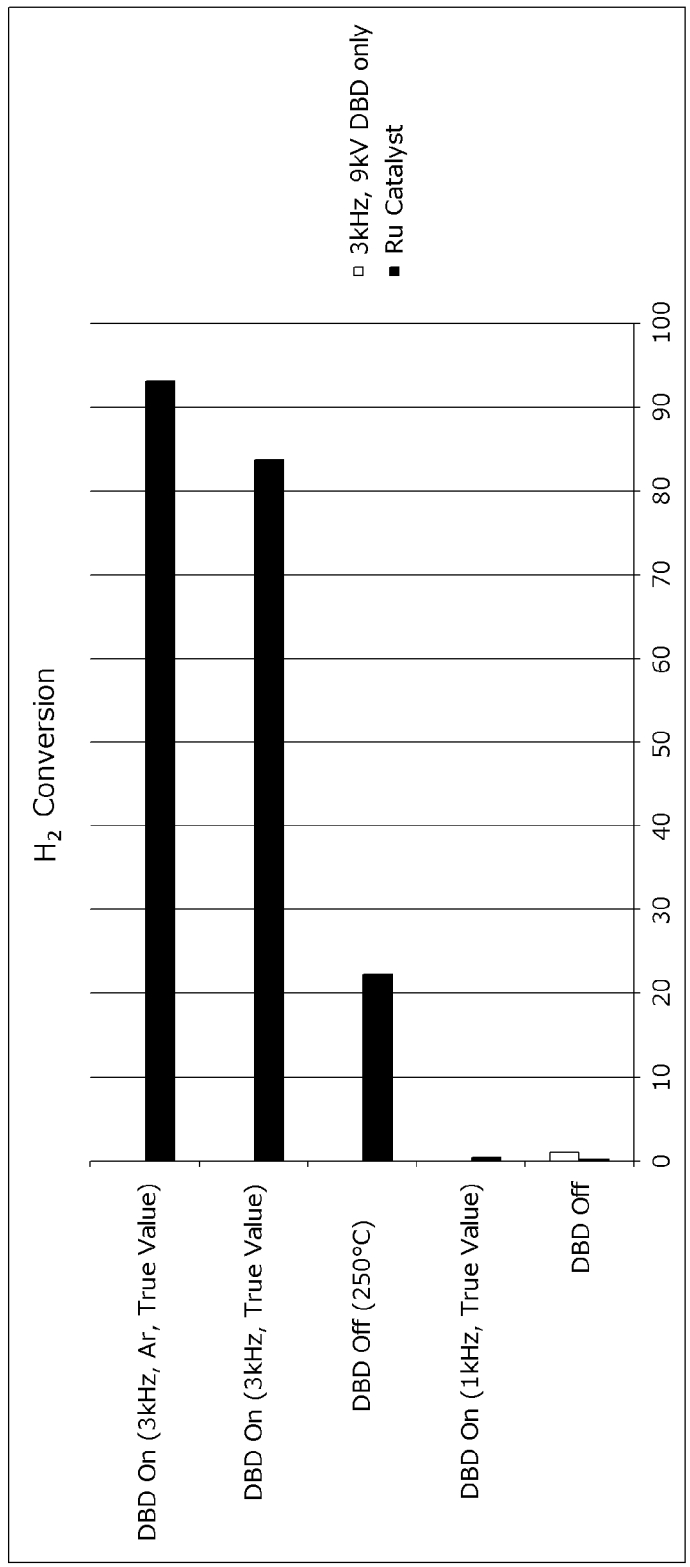
FIGS. 4 to 9 are graphs showing various test results for synthesizing methane gas using catalyst-DBD plasma.
Figure 5:
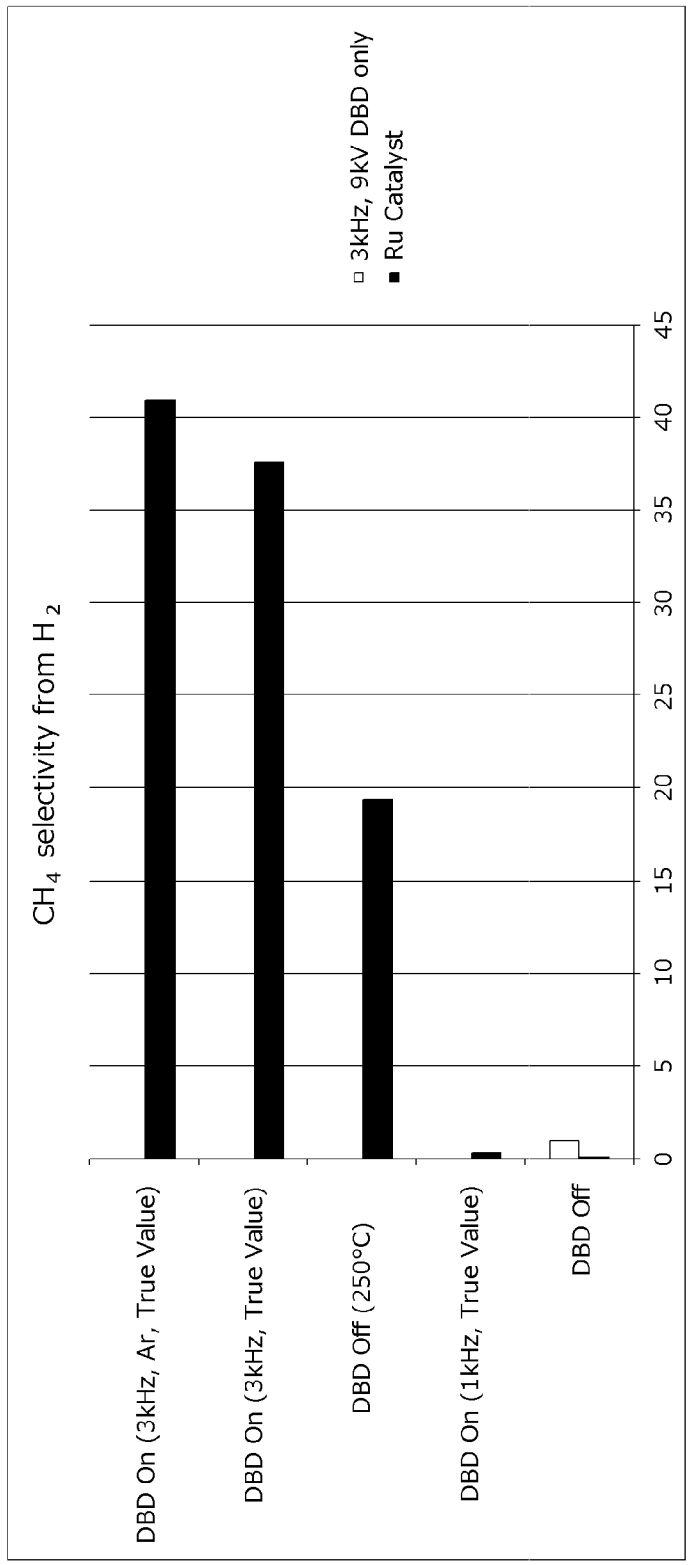
Figure 6:
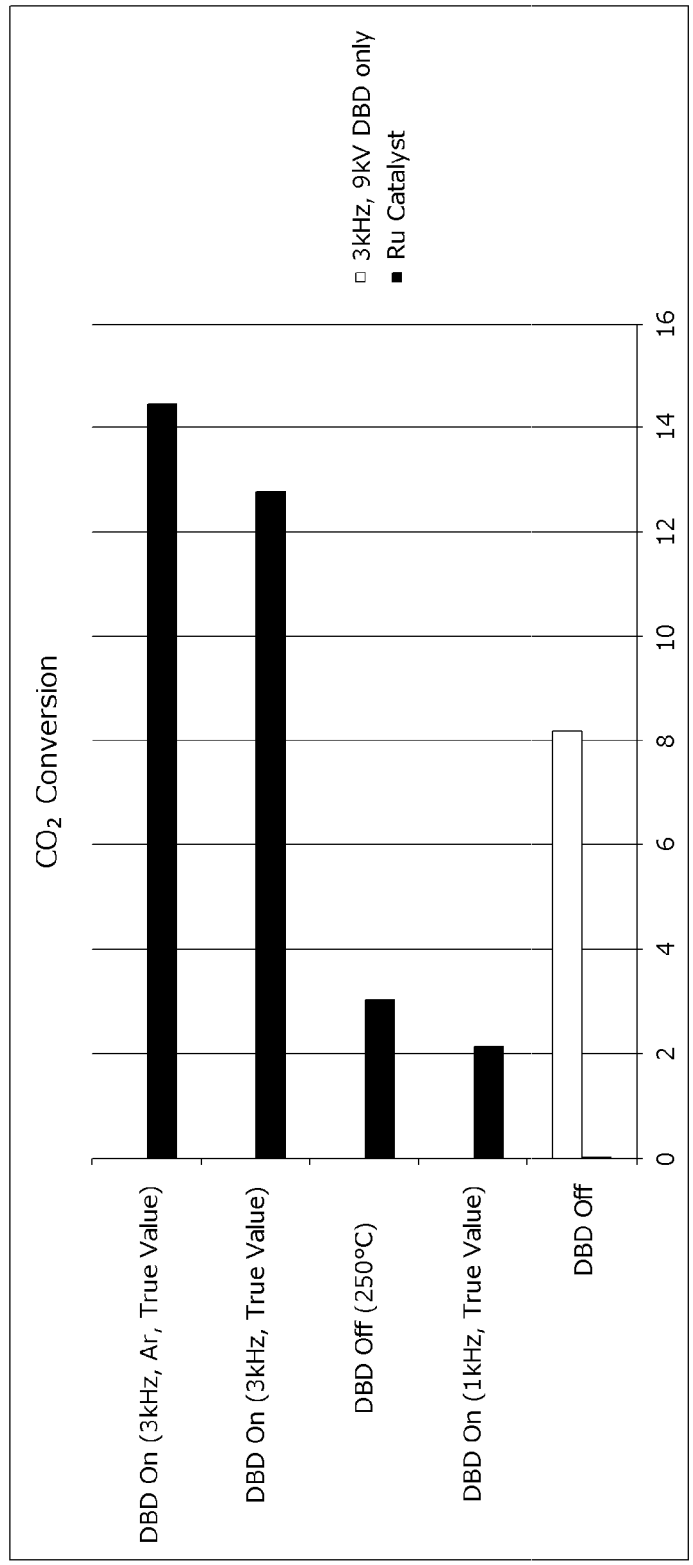
Figure 7:
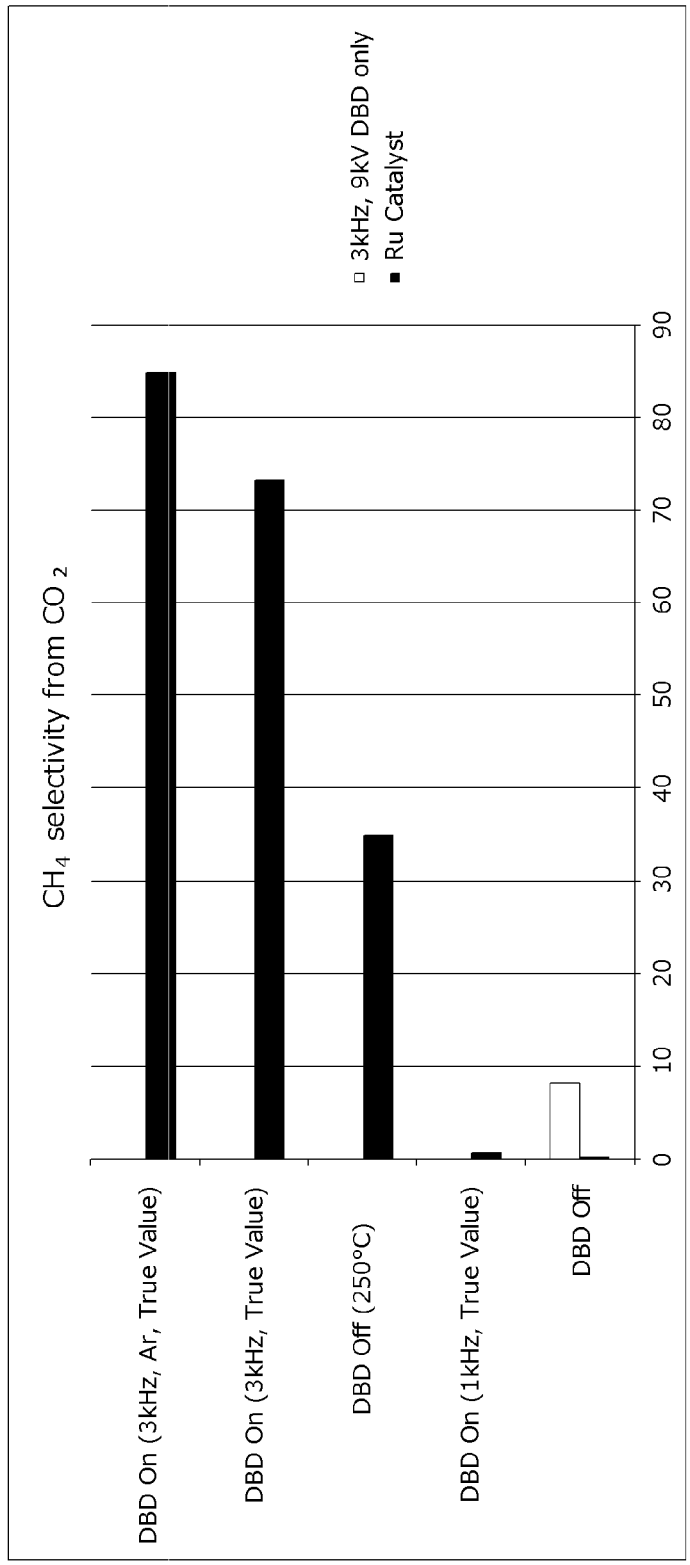
Figure 8:
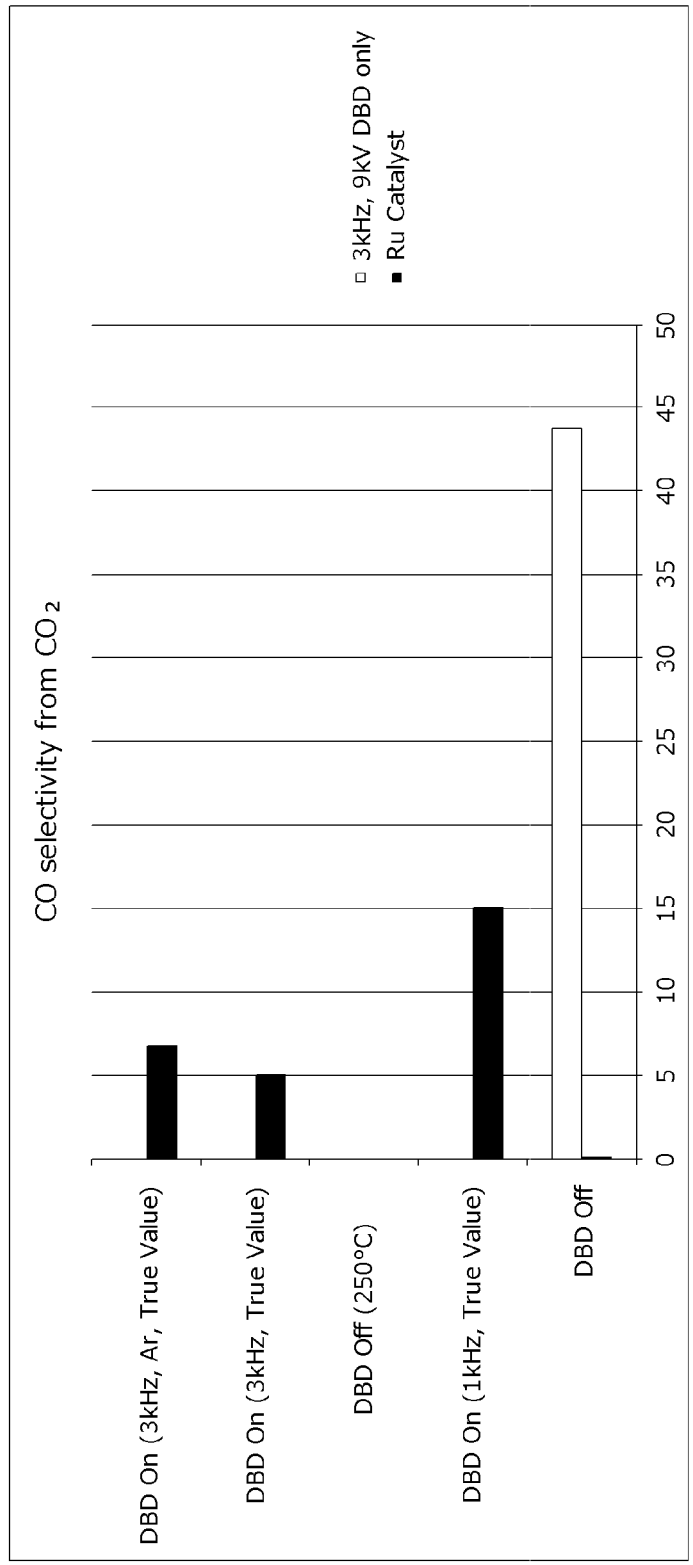
Figure 9:
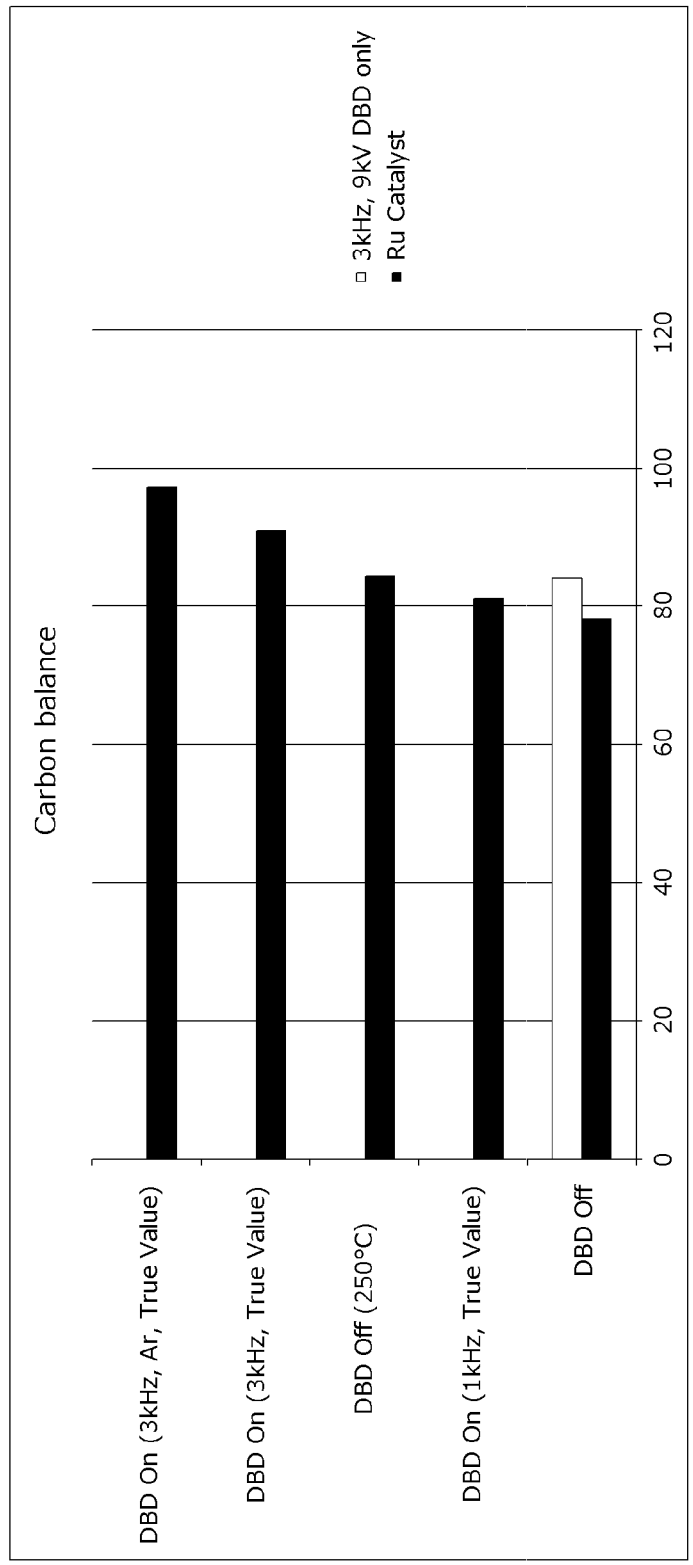

FIG. 3 shows a catalyst-DBD plasma hybrid reactor according to an embodiment of the present invention.

As shown in FIG. 3, the catalyst-DBD plasma hybrid reactor 120 is configured to include a quartz glass tube 121, an inner electrode 124, an outer electrode 125 and a catalyst 126.

The quartz glass tube 121 is made of a quartz glass material, and functions as a dielectric barrier while serving as the outer wall of the reactor.

The upper portion of the quartz glass tube 121 is provided with a gas inlet 122 for supplying carbon dioxide, hydrogen, nitrogen and argon gas, and the lower portion thereof is provided with an outlet 123 for exhausting the synthesized methane gas and other gas and liquid materials.

The gas inlet 122 and the outlet 123 may be provided by the combination with a pipe fitting made of stainless steel (SUS, Steel Use Stainless), and a tube made of Teflon may be connected thereto so as to facilitate the direction of supply or exhaustion of gas.

The inside of the quartz glass tube 121 is provided with the inner electrode 124 having a cylindrical rod shape, and the outer surface of the quartz glass tube 121 is wound with the outer electrode 125.

The inner electrode 124 is provided to generate DBD plasma, and the inner electrode 124 is made of stainless steel with a cylindrical shape so as to prevent corrosion from occurring, and the outer electrode 125 is provided in a manner in which iron (Fe) wire is wound in a spring shape for the sake of convenience.

The materials or shapes of the quartz glass tube 121, the inner electrode 124 and the outer electrode 125 are not necessarily limited thereto, and various materials or shapes suitable for forming DBD plasma may be used.

The catalyst 126 is loaded in the quartz glass tube 121 between the inner electrode 124 and the outer electrode 125.

The catalyst 126 may include a Group 8 metal element such as ruthenium (Ru) or rhodium (Rh). Particularly useful in an embodiment of the present invention is a Ru/γ-$Al_2O_3$ catalyst configured such that a gamma alumina support is impregnated with ruthenium (Ru). Here, the catalyst 126 is preferably loaded in the quartz glass tube 121 to the same length as that of the wound outer electrode 125, which is favorable for the formation of DBD plasma.

The apparatus 100 for synthesizing methane gas according to the embodiment of the present invention includes a high-voltage supplier 130 for applying high voltage to the inner electrode 124 and the outer electrode 125 so as to discharge plasma.

The high-voltage supplier 130 functions to increase alternating current (AC) input voltage in sine wave form generated from a function generator so as to supply the increased voltage to the inner electrode 124 and the outer electrode 125, whereby discharge for forming DBD plasma is performed.

The high-voltage supplier 130 is preferably a device for supplying AC power to the electrodes, and is not necessarily limited to the formation of AC DBD plasma but may be applied to non-equilibrium plasma or non-thermal plasma such as corona discharge, glow discharge, RF (radio frequency) discharge, and microwave discharge plasma.

As described above, the apparatus 100 for synthesizing methane gas from carbon dioxide and hydrogen at room temperature and atmospheric pressure according to the embodiment of the present invention is able to synthesize methane gas from carbon dioxide and hydrogen through an interaction between the catalyst 126 and the DBD plasma.

Specifically, radical production and ionization of carbon dioxide and hydrogen are promoted by the DBD plasma, and also, the synthesis of methane gas from carbon dioxide and hydrogen is promoted by the catalyst 126.

Here, DBD plasma discharge is conducted using, as the dielectric barrier, the quartz glass tube 121, which is the outer wall of the catalyst-DBD plasma hybrid reactor 120. When high voltage is applied to the inner electrode 124 and the outer electrode 125, DBD plasma is formed through the dielectric barrier discharge. Here, the DBD plasma discharge part 127 is formed around the catalyst 126 and the outer electrode 125. The region where the catalyst 126 is positioned is preferably formed so as to match the DBD plasma discharge part 5. In the zone where the catalyst-DBD plasma is formed, radical production and ionization of carbon dioxide and hydrogen by the DBD plasma are promoted, and simultaneously, the methanation of carbon dioxide and hydrogen using the catalyst is promoted.

A detailed description of methane synthesis in the catalyst-DBD plasma hybrid reactor 120 is given with reference to the description of FIG. 1.

The separation unit 130 includes a methane gas separation recovery part 132 for separating and recovering the synthesized methane gas via a separator 131, a gas separation part 133 for recovering and re-supplying carbon dioxide, hydrogen, nitrogen and argon, remaining without being used for the synthesis process, and a liquid separation part 134 for separating and removing a liquid hydrocarbon material.

Example 1

Catalyst

A catalyst was prepared through an incipient wetness impregnation process by impregnating a spherical gamma alumina ($\gamma$-$Al_2O_3$) support having a diameter of 1.1 mm with about 5.369 wt. % of ruthenium (Ru).

Catalyst-DBD Plasma Hybrid Reactor

A reactor was manufactured by combining a quartz glass tube and a pipe fitting made of stainless steel, and the quartz glass tube had a length of 400 mm, an outer diameter of 13 mm, an inner diameter of 11 mm, and a thickness of 1 mm, the diameter of the inner electrode was 3.15 mm, and the iron used for the outer electrode was a wire having a thickness of about 0.7 mm. Glass wool was inserted as a supporting base into the middle position of the reactor, and the catalyst was poured into a zone corresponding to about 50 mm of the length of the reactor in a longitudinal direction. The outer electrode was formed so as to match the 50 mm zone, and was wound in the shape of a spring having an average pitch of about 3 mm so that a DBD plasma discharge region was formed. The reactor was set up perpendicular to the ground and fixed, and gases were introduced into the gas inlet at the upper position of the reactor and subjected to a synthesis reaction, after which the resulting gas was exhausted from the outlet at the lower position thereof, passed through a water removal device (silica trap) and then fed into a gas analyzer.

Discharge for Forming DBD Plasma

AC input voltage in sine wave form having a frequency of 3 kHz generated from a function generator was increased to 9 kV and then supplied to the inner electrode and the outer electrode using a high-voltage supplier so that discharge was performed. In order to monitor and analyze the generated electrical characteristics, a high-voltage probe, a capacitor, and a digital oscilloscope were used.

Analysis of Produced Gas

The reaction product exhausted through the outlet of the reactor was dewatered using a silica trap, followed by analyzing the produced gas through gas chromatography capable of detecting hydrogen ($H_2$), nitrogen ($N_2$), carbon monoxide (CO), carbon dioxide ($CO_2$), methane ($CH_4$), acetylene ($C_2H_2$), ethylene ($C_2H_4$), ethane ($C_2H_6$), and propane ($C_3H_8$), all of which are in a gaseous phase.

TABLE 1

| | |
|---|---|
| Temperature | Room temperature (25° C.) |
| Pressure | Atmospheric pressure (1 atm) |
| Supplied gas | Nitrogen: 30 mL/min, hydrogen: 15 mL/min, carbon dioxide: 5 mL/min, argon: 30 mL/min |
| Catalyst | Ru/$\gamma$-$Al_2O_3$ (5.369 wt %) |
| Plasma | AC DBD plasma |
| Discharge conditions | 3 kHz, 9 kV, Sine |

Table 1 shows the processing conditions of Example 1. All processes were performed at room temperature and atmospheric pressure, without the use of additional heating and pressurization devices, and the gases used were nitrogen, hydrogen, carbon dioxide and argon, all having a high purity of 99.999%.

TABLE 2

| No. | Catalyst | Temperature | DBD plasma | Ar addition |
|---|---|---|---|---|
| 1 | x | 25° C. | x | x |
| 2 | Ru/$\gamma$-$Al_2O_3$ | 25° C. | x | x |
| 3 | Ru/$\gamma$-$Al_2O_3$ | 250° C. | x | x |
| 4 | Ru/$\gamma$-$Al_2O_3$ | 25° C. | 1 kHz, 9 kV, Sine | x |
| 5 | Ru/$\gamma$-$Al_2O_3$ | 25° C. | 3 kHz, 9 kV, Sine | x |
| 6 | Ru/$\gamma$-$Al_2O_3$ | 25° C. | 3 kHz, 9 kV, Sine | o (30 mL/min) |

Table 2 shows various test examples for synthesizing methane gas using catalyst-DBD plasma. In Test Example 3 (at a temperature of 250° C.), the surface of the reactor was measured using an IR thermometer to determine the dielectric heating temperature generated under DBD plasma discharge conditions of 3 kHz and 9 kV, from which dielectric heating of about 200 to 250° C. was evaluated to occur. This testing was conducted to obtain comparative data for a pure catalytic reaction without the DBD plasma discharge at the corresponding temperature.

FIGS. 4 to 9 are graphs showing various test results for synthesizing methane gas using catalyst-DBD plasma. Here, the term "conversion" refers to the ratio at which any material is supplied, processed and converted into another material, and the term "selectivity" refers to the ratio at which any specific material is more intensively formed among materials resulting from the conversion.

As shown in FIGS. 4 to 9, when pure DBD plasma was used alone in the absence of a catalyst under conditions of 3 kHz, 9 kV and a sine wave, hydrogen and carbon dioxide were converted at about 1.10% and about 8.21%, respectively, and the hydrogen-methane conversion selectivity was about 1.04% and the carbon dioxide-methane conversion selectivity was about 1.42%, which are regarded as very high. Also, the carbon dioxide-carbon monoxide conversion selectivity was high, namely 43.84%, from which the decomposition of carbon dioxide can be confirmed to mainly occur.

Under processing conditions in which only the pure catalytic reaction was carried out using a Ru catalyst without the application of DBD plasma at 250° C., hydrogen and carbon dioxide were converted at about 22.39% and about 3.06%, respectively, and the hydrogen-methane conversion selectivity was about 19.45% and the carbon dioxide-methane conversion selectivity was about 34.95%.

On the other hand, when DBD plasma generated under conditions of 3 kHz, 9 kV and a sine wave was discharged on the Ru catalyst, hydrogen and carbon dioxide were converted at about 83.88% and about 12.80%, respectively, and the hydrogen-methane conversion selectivity was about 37.64% and the carbon dioxide-methane conversion selectivity was about 73.30%, which are evaluated to be very high. Also, when DBD plasma discharge was performed by the addition of Ar gas, hydrogen and carbon dioxide were converted at about 93.30% and about 14.48%, respectively, and the hydrogen-methane conversion selectivity and the carbon dioxide-methane conversion selectivity were increased to about 41.00% and about 84.90%, respectively. In the former case, the total flow rate of the supplied gases was 50 mL/min, and in the latter case, argon was further added at 30 mL/min and thus the total flow rate was increased to 80 mL/min. In this case, as the gas flow rate in the reactor was increased, the time for which the supplied gases were exposed to the catalyst-DBD plasma was reduced, thus deteriorating reaction performance. However, in the present test results, plasma discharge energy was increased due to argon, thereby improving the conversion performance of carbon dioxide into methane. For the production of methane gas under the above two conditions, despite the processing at room temperature and atmospheric pressure, methane gas was produced at a maximum of 2.18 mL/min (in the absence of argon) and 2.65 mL/min (in the presence of argon). Furthermore, when argon was added, ethane ($C_2H_6$) and propane ($C_3H_8$) were formed in small amounts of about 0.0235% and about 0.0046%, respectively, in the reaction product.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

According to the present invention, a method and apparatus for synthesizing methane gas from carbon dioxide and hydrogen at room temperature and atmospheric pressure can contribute to environmentally friendly techniques as well as a reduction in global warming due to the removal of carbon dioxide, and can also be expected to be useful in a high-value-added industry for producing synthetic natural gas.

The invention claimed is:

1. A method of synthesizing methane gas, the method comprising:
    a gas supply step of supplying carbon dioxide ($CO_2$) gas, hydrogen ($H_2$) gas, nitrogen gas, and argon (Ar) gas to a reactor containing a ruthenium catalyst, wherein a total flow rate of the carbon dioxide gas, the hydrogen gas and the nitrogen gas is 50 mL/min, and the argon gas is added at 30 mL/min so that the total flow rate of the supplying gases is 80 mL/min;
    a methane gas synthesis step of synthesizing methane ($CH_4$) gas by forming dielectric barrier discharge (DBD) plasma on the ruthenium catalyst in the reactor at room temperature and atmospheric pressure; and
    a separation step, followed by the methane gas synthesis step, of separating the synthesized methane gas,
    wherein in the methane gas synthesis step, ionization of the carbon dioxide and the hydrogen is promoted by the dielectric barrier discharge (DBD) plasma, and synthesis of the methane gas from the carbon dioxide and the hydrogen is promoted by the ruthenium catalyst; and
    the whole method from the gas supply step to the separation step is free from using a heating or pressurization device.

2. The method of claim 1, wherein the ruthenium catalyst is a Ru/γ-$Al_2O_3$ catalyst prepared by impregnating a gamma-alumina support with ruthenium (Ru).

3. The method of claim 1, wherein the separation step comprises recovering the carbon dioxide g, the hydrogen gas, the nitrogen gas, and the argon gas which are not used for synthesizing the methane gas, and re-supplying the carbon dioxide gas, the hydrogen gas, the nitrogen gas and the argon gas which are recovered to the reactor.

4. The method of claim 1, wherein
    the flow rate of the nitrogen gas is 30 mL/min, the flow rate of the hydrogen gas is 15 mL/min, and the flow rate of the carbon dioxide gas is 5 mL/min; and
    the ruthenium catalyst is a Ru/γ-$Al_2O_3$ catalyst; and
    a dielectric barrier discharge (DBD) plasma is generated under conditions of 3 kHz, 9 kV and a sine wave.

* * * * *